(12) United States Patent
Lee et al.

(10) Patent No.: US 11,033,603 B2
(45) Date of Patent: Jun. 15, 2021

(54) METHOD FOR TREATING OCULAR DISEASES

(71) Applicant: ZIH YUAN TANG Biotechnology Co., Ltd., Taipei (TW)

(72) Inventors: Shoei-Sheng Lee, Taipei (TW); Ming-Jai Su, Taipei (TW); Lung-Jr Lin, Taichung (TW); Chao-Min Hsu, New Taipei (TW)

(73) Assignee: ZIH YUAN TANG BIOTECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 16/837,259

(22) Filed: Apr. 1, 2020

(65) Prior Publication Data
US 2020/0316165 A1    Oct. 8, 2020

Related U.S. Application Data

(60) Provisional application No. 62/828,616, filed on Apr. 3, 2019, provisional application No. 62/899,279, filed on Sep. 12, 2019.

(51) Int. Cl.
*A61K 38/15*    (2006.01)
*A61P 27/02*    (2006.01)

(52) U.S. Cl.
CPC .............. *A61K 38/15* (2013.01); *A61P 27/02* (2018.01)

(58) Field of Classification Search
CPC .................................. A61K 38/15; A61P 27/02
See application file for complete search history.

(56) References Cited

U.S. PATENT DOCUMENTS

| | | | | |
|---|---|---|---|---|
| 2010/0068141 A1* | 3/2010 | Kaushal | ................. | A61K 31/52 514/1.1 |
| 2014/0275091 A1* | 9/2014 | Serizawa | ............. | A61K 31/045 514/237.8 |
| 2014/0371158 A1* | 12/2014 | Chadli | ................... | A61K 38/15 514/19.4 |

* cited by examiner

*Primary Examiner* — Julie Ha
(74) *Attorney, Agent, or Firm* — Birch, Stewart, Kolasch & Birch, LLP

(57) ABSTRACT

The present invention provides a method for treating an ocular disease such as age-related macular degeneration (AMD), diabetic retinopathy (DR) or macular edema (ME), which comprises administering to a subject in need thereof a composition comprising a therapeutically effective amount of beauvericin.

5 Claims, 4 Drawing Sheets
(3 of 4 Drawing Sheet(s) Filed in Color)

METHOD FOR TREATING OCULAR DISEASES

CROSS REFERENCE TO RELATED APPLICATIONS

This application claims the benefit of and priority to U.S. Provisional Application Ser. No. 62/828,616, filed Apr. 3, 2019, and U.S. Provisional Application Ser. No. 62/899,279, filed Sep. 12, 2019, which are incorporated herein by reference in their entirety.

FIELD OF THE INVENTION

The present invention pertains to a method for treating ocular diseases, such as age-related macular degeneration, diabetic retinopathy and macular edema.

BACKGROUND OF THE INVENTION

Age-related macular degeneration (AMD) and diabetic retinopathy (DR) are the major causes of acquired blindness in developed countries and are characterized by pathologic posterior segment neovascularization (PSNV). Pathologic ocular angiogenesis, which includes PSNV, occurs as a cascade of events, progressing from the initial stimulus to the formation of abnormal new capillaries. Impelling reason for AMD, and DR is still unknown, however, production of various proangiogenic growth factors appears to be a common stimulus. It is found in tissues and fluids from patients with pathologic ocular angiogenesis. After starting the angiogenic cascade basement membrane and extracellular matrix capillaries degrade, and there is proliferation and migration of capillary endothelial cells. Endothelial outgrowths anastomose to form tubes with subsequent formation traversed lumen. The new capillaries commonly have increased vascular permeability or leaking due unformed barrier function, which can lead to tissue edema. Differentiation into a mature capillary is shown by the presence of a continuous basement membrane and normal endothelial connections between other endothelial cells and pericytes; however, this differentiation process is often impaired during pathologic conditions.

Macular edema is the major cause of vision loss in diabetic patients, whereas preretinal neovascularization (PDR) is the major cause of blindness practical. Diabetes mellitus is characterized by persistent hyperglycemia that causes reversible and irreversible pathologic changes in the microvasculature of various organs. Diabetic retinopathy (DR), therefore, is a disorder of retinal capillaries, which is manifested as a cascade of stages with increasing levels of severity and worsening forecasts for vision. Major risk factors reported for diabetic retinopathy include duration of diabetes, glycemic control and quality of the presence of systemic hypertension. DR commonly classified by 2 major clinical stages: non-proliferative diabetic retinopathy (NPDR) and proliferative diabetic retinopathy (PDR), where the term "proliferative" refers to the presence of preretinal neovascularization, as described above.

Macular degeneration, also known as age-related macular degeneration (AMD or ARMD), is a medical condition which may result in blurred or no vision in the center of the visual field. Early on there are often no symptoms; however, some people experience a gradual worsening of vision that may affect one or both eyes over time. There are some preventive methods including exercising, eating well, and not smoking while there is no cure or treatment that returns vision already lost. In the wet form, anti-VEGF medication injected into the eye or less commonly laser coagulation or photodynamic therapy may slow worsening. Supplements in those who already have the disease may slow progression.

There are currently no approved pharmacological therapies for the treatment AMD, DR and/or macular edema. There remains a need for developing medications for the treatment of said diseases.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

Figure 1:
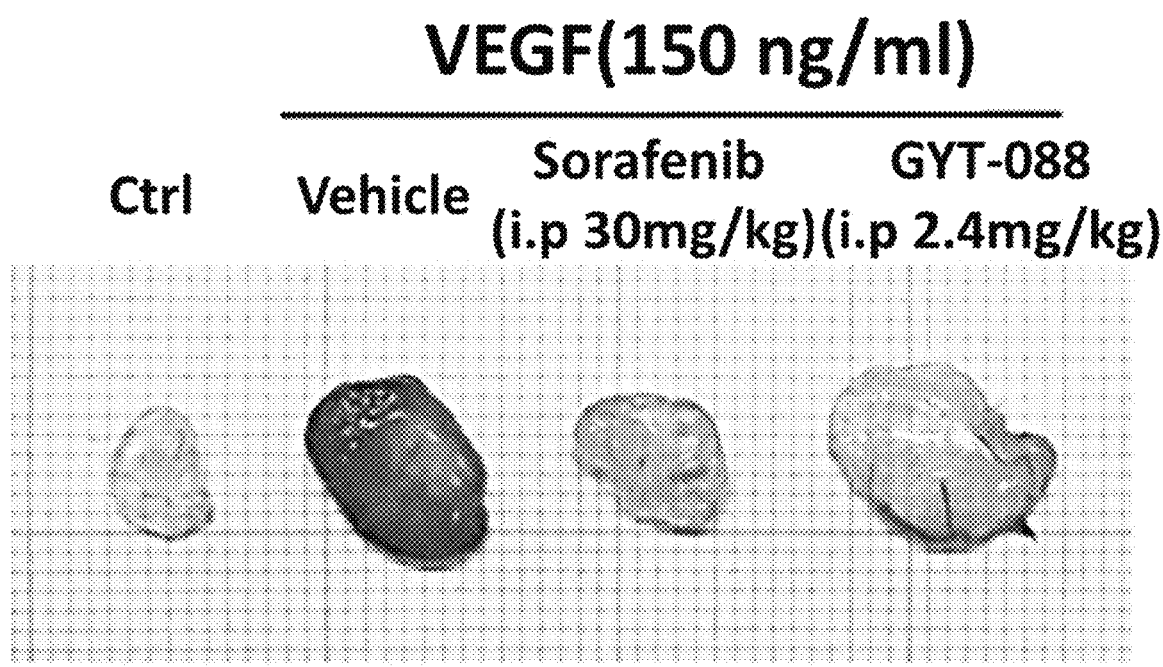

FIG. 1 provides the images showing the angiogenesis in the Matrigel plugs of the groups treated with Beauvericin (GYT-088, i.p. 2.4 mg/kg) and Sorafenib (i.p. 30 mg/kg) respectively.

Figure 2:
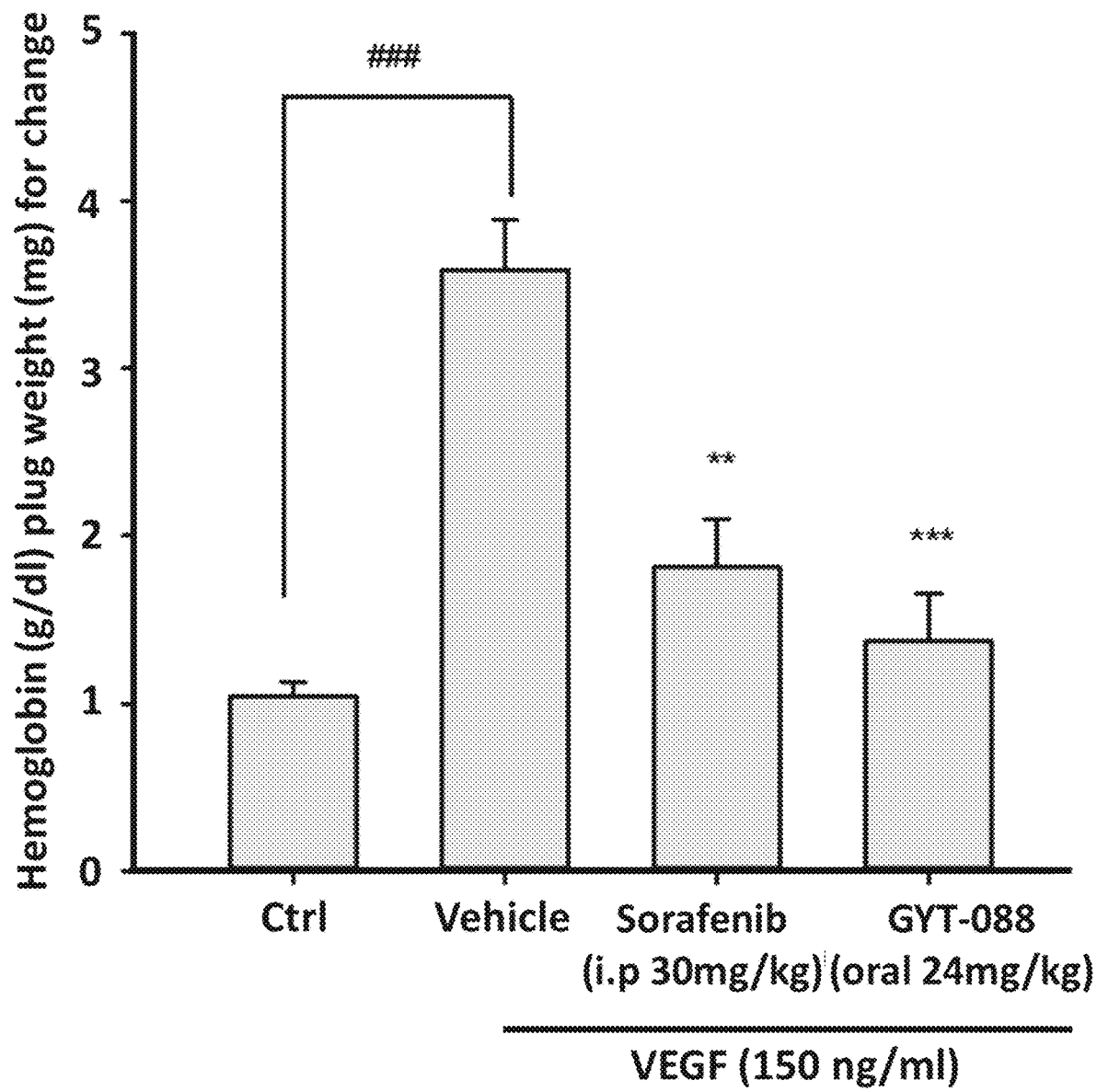

FIG. 2 provides a comparison of the hemoglobin level of each group, showing Beauvericin provided higher efficacy in inhibition of VEGF induced angiogenesis.

Figure 3:
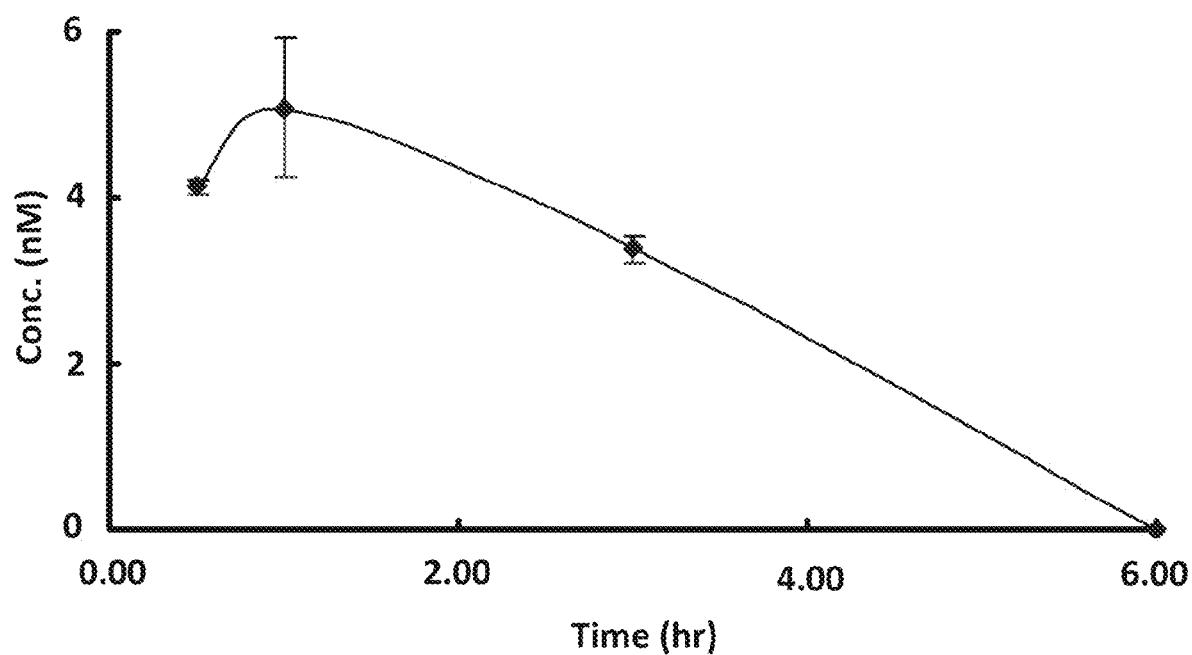

FIG. 3 shows that the test drug Beauvericin (GYT-088) according to the invention was observed in the eyes of the animal after oral administration of the GYT-008, indicating that the GYT-088 can be cross the blood-brain barrier (BBB) and particularly the blood-retinal barrier (BRB) to enter into the extravascular space of the retinal and vitreous body of the animal.

Figure 4:
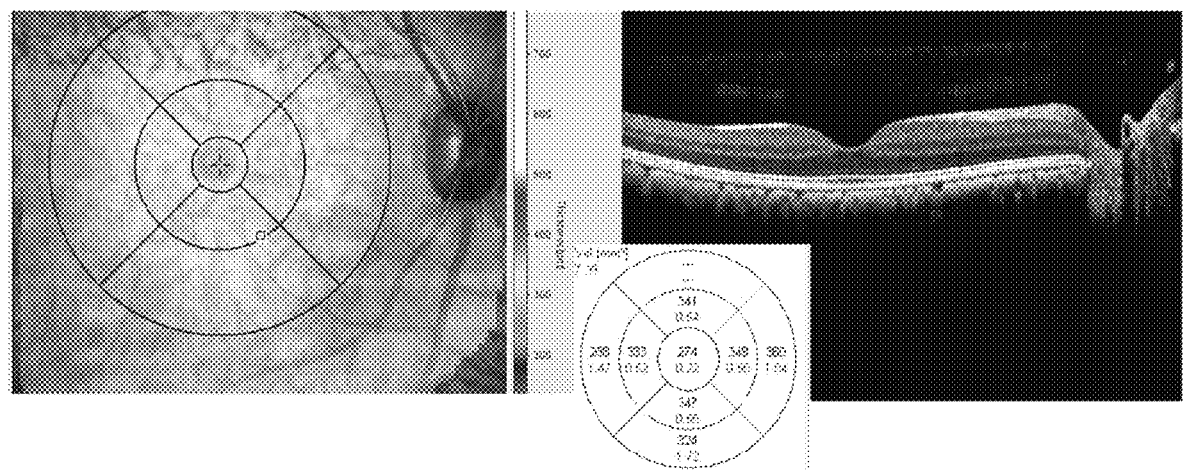

FIG. 4 provides the images showing the measurement of fovea and central macular of the animal.

SUMMARY OF THE INVENTION

It is unexpectedly discovered in the present invention that the compound, such as beauvericin (GYT-088 as named in the present invention), is effective in treatment of an ocular disease.

In one aspect, the present invention provides a method for treating an ocular disease, which comprises administering to a subject in need thereof a composition comprising a therapeutically effective amount of beauvericin having the following structural formula:

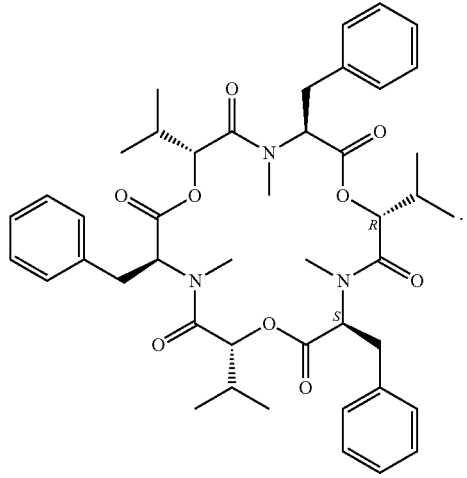

In further aspect, the invention also provides a use of beauvericin for preparing a medicament for treating an ocular disease.

In yet aspect, the invention provides a pharmaceutical composition for use in treating an ocular disease, which comprises in association with one or more pharmaceutically acceptable carriers and a therapeutically effective amount of beauvericin.

In one embodiment, the ocular disease is caused by eyes regression of neovascularization.

In some examples of the invention, the ocular disease is age-related macular degeneration (AMID), diabetic retinopathy (DR) or macular edema (ME). In preferable examples of the invention, the ocular disease is non-proliferation diabetic retinopathy (NPDR) or wet age-related macular degeneration (wet AMD).

It is to be understood that both the foregoing general description and the following detailed description are exemplary and explanatory only and are not restrictive of the invention.

DETAILED DESCRIPTION OF THE INVENTION

Unless defined otherwise, all technical and scientific terms used herein have the same meaning as commonly understood by a person skilled in the art to which this invention belongs.

In the present invention, some compounds were first discovered to have significant effect in treating an ocular disease such as age-related macular degeneration (AMD), diabetic retinopathy (DR) or macular edema (ME).

The present invention provides a method for treating an ocular disease, comprising administering to a subject in need thereof a composition comprising a therapeutically effective amount of beauvericin, which is a cyclohexadepsipeptide consisting of three L-N-methylphenylalaline coupled with three D-2-hydroxyisovaleric acid, and has a structural formula:

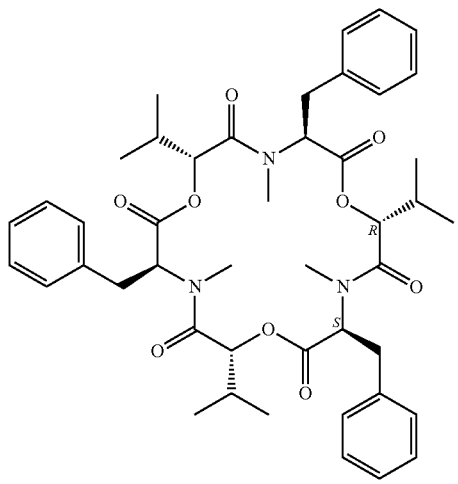

The compounds in the present invention, such as beauvericin, may be synthesized, or isolated from fungi, such as *Cordyceps cicadae, Cordyceps sobolifera, Cordyceps cicaicola* and *Isaria fumosorosea*, according to conventional technologies or methods.

In the invention, the compound is proved to be effective for treating an ocular disease through inhibition of VEGF induced angiogenesis.

In one embodiment, the ocular disease is caused by eyes regression of neovascularization. Some examples of the ocular disease include age-related macular degeneration (AMD), diabetic retinopathy (DR) and macular edema (ME). In preferable examples of the invention, the ocular disease is non-proliferation diabetic retinopathy (NPDR) or wet age-related macular degeneration (wet AMD).

The term "therapeutically effective amount" as used herein refers to an amount of a compound or pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

For use in therapy, the therapeutically effective amounts of the compound is formulated as a pharmaceutical composition for administration. Accordingly, the invention further provides a pharmaceutical composition comprising a therapeutically effective amount of the compound beauvericin and one or more pharmaceutically acceptable carriers.

The term "pharmaceutically acceptable carriers" used herein refers to a carrier(s), diluent(s) or excipient(s) that is acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation.

According to the invention, the pharmaceutical composition may be adapted for administration by any appropriate route, including but not limited to oral, rectal, nasal, topical, vaginal, or parenteral route. In one particular example of the invention, the pharmaceutical composition is formulated for oral administration. Such formulations may be prepared by any method known in the art of pharmacy.

The present invention is further illustrated by the following examples, which are provided for the purpose of demonstration rather than limitation.

EXAMPLES

Example 1

In Vivo Matrigel Plug Angiogenesis Assay

Matrigel plug is made from a gelatinous protein mixture secreted by Engelbreth-Holm-Swarm (EHS) mouse sarcoma cells (produced and marketed by Corning Life Sciences and BD Biosciences). Matrigel resembles the complex extracellular environment found in many tissues and is used by cell biologists as a substrate (basement membrane matrix) for culturing assay.

The test animals were 5 to 8-week-aged B57l/6 mice. The Matrigel was mixed with PBS at a ratio of 4:1 to obtain the Matrigel plug. The mice were administered with the Matrigel plugs containing 30 IU heparin and VEGF 150 ng/ml (500 ul/mouse), and then divided into four groups (4 mice in one group), treated with Beauvericin i.p. or orally (GYT-088 Group), Sorafenib (Sorafenib Group) as a positive control, VEGF alone (Vehicle), and without any treatment (Ctrl). After one day, the animals were administered with the sorafenib i.p. at a dosage of 30 mg/kg or Beauvericin i.p. at a dosage of 2.4 mg/kg (0.1c.c./mice/day), or were orally administered with the Beauvericin at a dosage of 24 mg/kg once per day for six days. On Day 7, the animals were sacrificed and the Matrigel plugs were taken out for observation of angiogenesis. The hemoglobin of each mouse was also measured by Drabkin's reagent kit.

The results were given in FIGS. 1 and 2. As shown in FIG. 1, the VEGF induced angiogenesis was inhibited in the groups treated with Beauvericin i.p. (GYT-088 Group) or Sorafenib (Sorafenib Group) as a positive control. As shown in FIG. 2 showing the hemoglobin levels as measured, beauvericin provided higher efficacy in inhibition of VEGF induced angiogenesis.

In conclusion, beauvericin provided an efficacy in inhibition of angiogenesis, even better than Sorafenib.

Example 2

Evaluation of Efficacy of beauvericin at different doses for 60 days on improving naturally-occurring diabetic macular edema in rhesus monkeys, providing a basis for clinical trial dose design and safety study.

*Macaca mulatta* (Rhesus Macaque) are used in the evaluation.

Primary Endpoints:

Retinal Thickness by OCT. To Quantify Retinal Thickness Before and after Treatment.

Retinal thickness is evaluated by 2 methods using OCT: (1) at the fovea and 1.5 mm on either side of it (three point method), and (2) using a 52-point grid to determine the fraction of macula that had thicknesses in different thickness groupings (250-300, 301-350, 351-400 μm, etc.). This method was developed by the Primed team in collaboration with Prof. Dr. Timothy Kern, a renowned diabetic retinopathy expert from Case Western Reserve University. Refer to the ARVO 2018 Poster. Assessment of macular thickening in spontaneously diabetic rhesus monkeys.

Secondary Endpoints and Safety Parameters:

(1) Fundus photography (FP). To detect changes of hemorrhage, exudate or vessel lesion before and after treatment; and (2) Drug effect on metabolism and lipid profiles, liver and kidney function.

Non-human primates (NHPs) are extremely similar to humans in physiological function and structure of eyes. PriMed has a unique sizable NHP population (n=~1500) with spontaneous metabolic disorders with historical clinical/metabolic data for 5 years, including fasting plasma glucose (FPG), insulin resistance, body mass index (BMI), triglyceride (TG), total cholesterol (TC), low-density lipoprotein cholesterol (LDL-c) and high-density lipoprotein cholesterol (HDL-c). Color Doppler Ultrasound, Kowa fundus camera, Heidelberg OCT, slit lamp and ophthalmoscope are used to diagnose diabetic status of NHPs, demonstrating that the disease characteristics of spontaneous diabetic macular edema of rhesus monkeys are very similar to those of clinical patients, manifested in vascular leakage, retinal thickening, exudation, or bleeding. Spontaneous DME rhesus monkey provides an ideal model for human Diabetic Macular Edema (DME)/Diabetic Retinopathy (DR) research and new drug development.

Inclusion Criteria (1) Female, age 13-18 years (equals to 40-60 years old in human adults), 6-7 kg;

(2) Diabetic duration: over 3 years;

(3) DME of single/both eyes;

(4) DME: the retinal thickness measured by Heidelberg Spectralis OCT in recent half year and diagnosed by FP/FFA with Kowa VX-20 Fundus Camera;

(5) CRT≥260 μm (Central Foveal Thickness) and/or Average Thickness of ETDRS regions≥319 μm. (Retinal Thickening is defined by Mean and SD of CRT and ETDRS thickness of normal monkeys). The retinal thickening is defined as thickness that exceeded the normal mean by 2 standard deviations. Nondiabetic monkey: Average thickness of the retina in nondiabetic animals was 192±11 μm at the fovea, and 307±15 and 328±13 measured at a distance of 1.5 mm from fovea on the temporal and nasal sides, respectively. This method was developed by the Primed team in collaboration with Prof. Dr. Timothy Kern, a renowned diabetic retinopathy expert from Case Western Reserve University. Refer to the ARVO 2018 Poster. Assessment of macular thickening in spontaneously diabetic rhesus monkeys; and (6) with/without vessel leakage or non-perfusion area.

Exclusion Criteria (1) Stage 3 Hypertension and above;

(2) Active ocular or systemic inflammation or infection; Intraocular hypertension: IOP>21 mmHg;

(3) Laboratory tests indicates significantly impaired renal or hepatic function;

(4) Any other disease history that might affect efficacy.

Group Sizes 6 spontaneous DME rhesus monkeys (with medical record within one year) will be provided and 4 out of 6 monkeys will be enrolled in the Pre-study period (four weeks) for FA, FP, OCT and slit lamp examination as well as blood biochemistry before treatment. 4 Monkeys will be divided into two groups based on retinal thickness by OCT:

(1) Group 1, vehicle group, N=1;

(2) Group 2, test article group, N=3;

(Route of administration: oral administration, once a day; Dosage: TBD).

Outcome Measurements:

Primary Efficacy Parameters:

Retinal thickness includes CST and ETDRS thickness. Once pre-dose and post-dose D14 and D30 and D60; whether to add detection on D45 will be determined according to the results of D14 and D30.

Secondary Efficacy Parameters and Safety Parameters:

(1) Fundus photography: once pre-dose as baseline and post-dose D30, D60, 3 times in total;

(2) FFA: once pre-dose as baseline;

(3) TOP and blood pressure measurement: once pre-dose and once post-dose, 2 times in total;

(4) Clinical signs of eyes evaluated by daily cage-side observation;

(5) Dysmetabolic parameters, liver and kidney function measurement: FPG, FRA, LDL, HDL, TC, TG: once pre-dose and post-dose D14, D30, D45 and D60;

(6) Slit Lamp: once pre-dose and once post-dose, 2 times in total;

(7) Body weight: once pre-dose and post-dose D30 and D60;

(8) Food intake/clinical observation: including abnormal signs, symptoms and behaviors, once a day.

Fundus Photography (FP) and Fluorescein Fundus Angiography (FFA)

(1) Frequency: FFA was performed once before administration.

(2) Instrument: KOWA VX-20.

(3) Purpose: To examine retinal vessel damage and leakage.

(4) FFA image acquisition protocol:

Prior to image acquisition, animals were anesthetized with intramuscular injection of Ketamine:Xylazine mix (1:1, 8 mg/kg Ketamine). 2 drops of Tropicamide Phenylephrine Eye Drop were applied to each eye after anesthesia for pupil dilation. After being anesthetized, animals were placed in a dark room until pupil diameter was greater than 6 mm. A self-retaining eyelid spectrum was placed in the eye. The posterior pole of fundus of the major eye for photography was well focused.

(5) Timer started when 10% fluorescein sodium (Alcon Laboratories, USA) was injected via femoral vein at a dose of 0.075 mL/kg. A series of photographs of the posterior pole were taken for the major eye once a second in the first 30 seconds and once 2-3 seconds in the next 30 seconds. Photographs were taken for both eyes at 5 minutes and 10-15 minutes.

Results

Vehicle group: #6189 showed mild NPDR before dosing. No significant changes were found before and after dosing by FP, as shown in Table 1. GYT-088 group: #251, #2003 and #3536 showed mild or moderate NPDR. Characteristics of NPDR in #2003 were improved at D28 after dosing by FP. No significant changes were found before and after dosing in other animals at any time points by FP, see Table 1.

TABLE 1

NPDR Related Changes after Treatment

| Group | ID | Baseline | D28 | D56 |
|---|---|---|---|---|
| Vehicle (n = 1) | 6189 | FP images show arteries are tortuous, narrow and reflective. The second branch vein above optic disc is tortuous at both eyes. FFA images show there are IRMA at superior and inferior sides at 1 PD from optic disc. There are small non-perfusion areas at retina. | FP images show in both eyes arteries are tortuous, narrow and reflective. The second branch vein above optic disc is tortuous. Punctate degeneration is found at the temporal side of macula. | FP images show in both eyes arteries are tortuous, narrow and reflective. The second branch vein above optic disc is tortuous. Punctate degeneration is found at the temporal side of macula. |
| GYT-088 (n = 3) | 251 | FP images show distal veins are segmentally narrow, mildly tortuous and dilated. FFA images show there are small non-perfusion areas at both eyes. Local fluorescein leakage of micro-vessels or small vessels at the middle and late stage of angiography. | FP images show distal veins are segmentally narrow, mildly tortuous and dilated. | FP images show distal veins are segmentally narrow, mildly tortuous and dilated. |
| | 2003 | FP images show linear and punctate hemorrhage at the temporal side of optic disc at OD. Flaky hemorrhage at distal vein at the superior temporal side of optic disc and at bifurcation of vein at superior nasal side of optic disc. FFA images show there are small non-perfusion areas at both eyes. Local fluorescein leakage of microvessels or small vessels at the middle and late stage of angiography. | There are no abnormalities related to DR | Flaky hemorrhage at two locations at inferior vessel arch of OD and at nasal side of optic disc of OS. |
| | 3536 | FP images show several white punctate degeneration at both eyes. FFA images show there are small non-perfusion areas at both eyes. Local fluorescein leakage of micro-vessels or small vessels at the middle and late stage of angiography. | FP images showed no DR-related abnormalities in both eyes. | FP images showed no DR-related abnormalities in both eyes. |

The results were provided in FIG. 4. On Day 14 of administration, it was found in the test animal #2003 (NPDR Group) that the central macular thickness (CMT) was changed from 204 μm and 210 μm in left and right eyes to 197 μm and 202 μm, reduced by 7 μm and 8 μm, respectively; and the fovea thickness from 257 μm and 260 μm in left and right eyes to 249 μm and 251 μm, reduced by 8 μm and 9 μm, respectively. On the other hand, it was found in the animal #6189 administered with the vehicle (Vehicle Group) that the change in either the central macular thickness or the fovea thickness ranged in ±2 μm, as normally found in the normal animals. At Day 56 of the administration, the central macular thicknesses were reduced by 6 μm and 8 μm, and the macular thicknesses were reduced by 3 μm and 5 μm in left and right eyes respectively. Therefore, it was concluded that GYT-088 provided an efficacy in Diabetic Macular Edema.

TABLE 2

The changes of thickness in Diabetic Macular Edema (DME)

| GYT-008 | | Macular Central Thickness (μm) | | Fovea Thickness (μm) | |
|---|---|---|---|---|---|
| Group | Day of Administration | Left eye | Right eye | Left eye | Right eye |
| 6189 (Vehicle) | Baseline | 216 | 210 | 270 | 265 |
|  | D14 | 215 | 208 | 268 | 267 |
|  | D28 | 214 | 209 | 269 | 263 |
|  | D56 | 216 | 208 | 271 | 266 |
| 2003 (NPDR) | Baseline | 204 | 210 | 257 | 260 |
|  | D14 | 197 | 202 | 249 | 251 |
|  | D28 | 199 | 206 | 253 | 255 |
|  | D56 (Double dosing) | 200 | 202 | 254 | 255 |

While this specification contains many specifics, these should not be construed as limitations on the scope of the invention or of what may be claimed, but rather as descriptions of features specific to particular embodiments or examples of the invention. Certain features that are described in this specification in the context of separate embodiments or examples can also be implemented in combination in a single embodiment.

What is claimed is:

1. A method for treating an ocular disease, which comprises administering to a subject in need thereof a composition comprising a therapeutically effective amount of beauvericin:

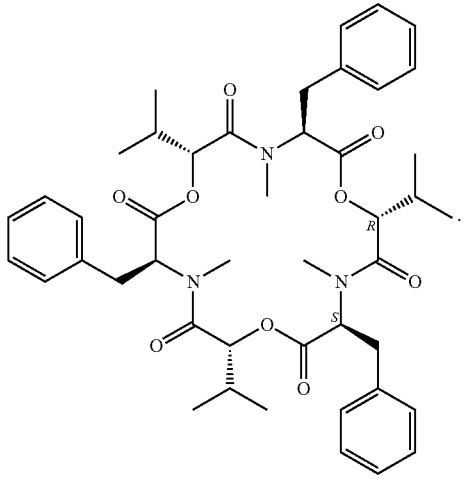

2. The method of claim 1, wherein the ocular disease is caused by eyes regression of neovascularization.

3. The method of claim 1, wherein the ocular disease is age-related macular degeneration (AMD), diabetic retinopathy (DR) or macular edema (ME).

4. The method of claim 3, wherein the age-related macular degeneration (AMD) is wet age-related macular degeneration (wet AMD).

5. The method of claim 3, wherein the diabetic retinopathy (DR) is non-proliferation diabetic retinopathy (NPDR).

* * * * *